United States Patent [19] [11] 4,402,853
Brocklehurst et al. [45] Sep. 6, 1983

[54] STABLE PEROXIDE COMPOSITION AND METHOD OF PREPARATION THEREOF

[75] Inventors: Peter Brocklehurst, Chappletown Nr. Sheffield; Angus S. Ferguson, Sheffield, both of England

[73] Assignee: Sterling Drug Inc., New York, N.Y.

[21] Appl. No.: 365,248

[22] Filed: Apr. 5, 1982

[51] Int. Cl.³ .................... C07C 179/00; C11D 3/39
[52] U.S. Cl. .............................................. 252/186.26
[58] Field of Search ............... 252/186.26, 95; 8/111; 568/559, 701

[56] References Cited

U.S. PATENT DOCUMENTS 3,494,786  2/1970  Nielsen ................................ 252/95
3,494,787  2/1970  Lund et al. .......................... 252/95
3,622,366 11/1971  Piester ................................. 252/95
3,639,285  2/1972  Nielsen ......................... 252/186.26
4,100,095  7/1978  Hutchins et al. ............. 252/186.26
4,126,573 11/1978  Johnson ....................... 252/186.26

FOREIGN PATENT DOCUMENTS 1456591 11/1976  United Kingdom .
1456592 11/1976  United Kingdom .

OTHER PUBLICATIONS

Research Disclosure, Sep. 1974, No. 12510, pp. 4–6.

Primary Examiner—Irwin Gluck
Attorney, Agent, or Firm—Frederik W. Stonner; B. Woodrow Wyatt; Paul E. Dupont

[57] ABSTRACT

A stable succinyl peroxide composition comprising in solid particulate form a mixture of succinyl peroxide, a water-soluble dehydrating agent which is unreactive to succinyl peroxide, e.g., magnesium or sodium sulfate, and water, the water being bound to the dehydrating agent as water of hydration; and a method of preparation thereof comprising mixing a paste of succinyl peroxide in water with a water soluble dehydrating agent, the dehydrating agent being mixed with the succinyl peroxide paste in an amount and for a time sufficient to bind all of the water in the paste and provide a dry mixture.

33 Claims, 1 Drawing Figure

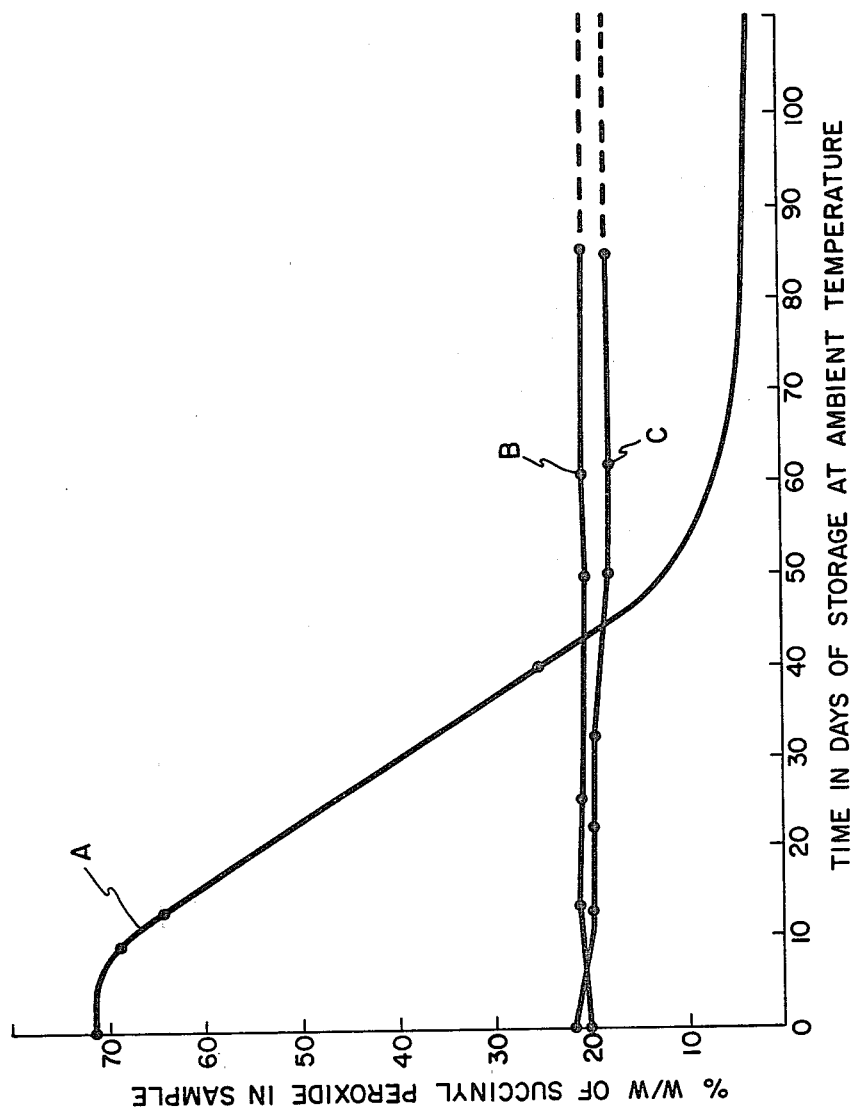

STABLE PEROXIDE COMPOSITION AND METHOD OF PREPARATION THEREOF

BACKGROUND OF THE INVENTION

1. Field of the Invention

The invention relates to a stable succinyl peroxide composition and a method of preparation thereof.

2. Description of the Prior Art

Succinyl peroxide, which is also known as disuccinyl peroxide or succinic acid peroxide is a compound of the formula:

$$(HOOC.CH_2.CH_2.CO)_2O_2$$

Succinyl peroxide is known for use as a polymerization initiator, as a deodorant and as an antiseptic. In the past the compound has been sold in the dry powder form for use as a polymerization initiator, but it was found that the dry powder is friction sensitive and, under certain circumstances, could explode. In order to overcome this problem succinyl peroxide is currently marketed as a 70 percent by weight paste in water.

However, succinyl peroxide as a paste in water is unstable at ambient temperatures, the peroxide decomposing by hydrolysis, and stability can only be ensured by storing the paste under refrigerated conditions, typically at $-10°$ C. It will be appreciated that the need to store and transport the paste under refrigerated conditions is a significant disadvantage, especially when the succinyl peroxide is required for use in applications where for instance relatively small unit doses of the peroxide are to be stored before use, for example, as an antiseptic.

The encapsulation of perphthalic acids in protective coatings of hydrated or partially hydrated salts such as partially hydrated and hydrated magnesium and sodium sulfate is described in the prior art, e.g., see U.S. Pat. Nos. 3,494,786 and 3,494,787 to Nielsen, and U.S. Pat. No. 3,622,366 to Piester.

U.S. Pat. No. 3,639,285 to Nielsen discloses that the stability of monoperphthalic acids can be substantially improved by incorporating therewith certain alkali metal and alkali earth metal salts such as anhydrous magnesium and sodium sulfate.

British Pat. No. 1,456,591 to The Procter & Gamble Company describes bleaching compositions of excellent storage stability comprising a specified peroxyacid material, a peroxyacid-stabilizing agent mixture consisting essentially of a specified proportion of magnesium sulfate and a particular alkali metal sulfate, and a specified amount of bound water of hydration.

British Pat. No. 1,456,592 to The Procter & Gamble Company describes peroxy bleaching granules comprising, in specified amounts, a normally solid, organic, water-soluble peracid admixed with a bleach-stabilizing agent such as magnesium or sodium sulfate, water of hydration, and a fatty alcohol coating material.

Research Disclosure, September, 1974, No. 12510, pp. 4-6, teaches the stabilization of a peroxygen compound selected from p-nitroperbenzoic acid, diperazelaic acid and m-chloroperbenzoic acid by contacting spray droplets of the peroxygen compound with a fluidized bed of magnesium sulfate particles having a moisture content of less than 10%, and mixing for a time sufficient for the water content of the spray droplets to be bound by the magnesium sulfate to give a substantially dry and free-flowing magnesium sulfate coated peroxygen compound.

None of the foregoing references describe stable succinyl peroxide compositions.

SUMMARY OF THE INVENTION

It has now been found surprisingly that an intimate mixture of succinyl peroxide, a water-soluble dehydrating agent which is unreactive to succinyl peroxide, and water, the water being bound to the dehydrating agent as water of hydration, provides a composition which is stable on storage at ambient temperature and which does not possess the friction sensitivity of dry, powdered succinyl peroxide.

Therefore in one aspect, the invention provides a stable succinyl peroxide composition comprising in particulate solid form a mixture of succinyl peroxide, a water-soluble dehydrating agent which is unreactive to succinyl peroxide, and water, the water being bound to the dehydrating agent as water of hydration.

In another aspect, the invention provides a method for preparing a stable succinyl peroxide composition comprising in particulate solid form a mixture of succinyl peroxide, a water-soluble dehydrating agent which is unreactive to succinyl peroxide, and water, the water being bound to the dehydrating agent as water of hydration, which method comprises mixing a succinyl peroxide paste consisting of succinyl peroxide and water with a water-soluble dehydrating agent selected from the group consisting of anhydrous dehydrating agent and partially hydrated dehydrating agent, the dehydrating agent being mixed with the succinyl peroxide paste in an amount and for a time sufficient to bind all the water in the paste and provide a dry mixture.

The compositions of the invention are microbiocidal and are useful for preparing aqueous solutions having utility as disinfecting and/or sterilizing and/or antiseptic agents.

DETAILED DESCRIPTION OF THE INVENTION INCLUDING THE PREFERRED EMBODIMENTS

In the compositions of the invention, the dehydrating agent, as more fully defined hereinbelow, must be water-soluble, sufficiently inert not to react with the succinyl peroxide, and have bound thereto water as water of hydration, preferably water of crystallization. The dehydrating agent should be such that a use-solution of the composition in water has a pH below 5, and in fact should not materially alter the pH of succinyl peroxide in solution. Essentially all of the water present in the compositions must be bound to the dehydrating agent as water of hydration. The relative amounts of water and dehydrating agent in the compositions can be such that the dehydrating agent is either in partially hydrated form or approaches the fully hydrated form. It should be understood however that as used herein in describing the compositions of the invention, the term dehydrating agent refers to such agent on an anhydrous basis. Thus, the parts by weight of dehydrating agent in the compositions as specified herein are on an anhydrous basis.

In practicing the method of the invention, the dehydrating agent to be employed can be either in anhydrous or partially hydrated form. Although any dehydrating agent which meets the criteria of water-solubility and inertness to succinyl peroxide as specified hereinbefore is suitable, preferred dehydrating agents employed in the method of the invention are inorganic dehydrating agents, especially anhydrous and partial hydrates of sodium and magnesium sulfate. Of these, magnesium sulfate is the more preferred since it combines more rapidly and more firmly with water and thus leads to more stable compositions. A preferred form of magnesium sulfate is the partially hydrated form having the formula $MgSO_4.nH_2O$, where n has a value of 1 to 4, preferably 1 to 2. Since the dehydrating agent acts to remove water from the paste, i.e., by binding the water as water of hydration, the level of hydration, if any, of the dehydrating agent initially employed in the method of the invention will of course be below that in the final composition of the invention. Thus, in the case of hydrates of magnesium sulfate, in the final compositions, in the formula $MgSO_4.nH_2O$, n will have values greater than the corresponding values for n specified above, and typically can have a value of from 2 to less than 7, preferably 2 to 3, i.e., for each mole of magnesium sulfate in the final composition there can be from 2 to less than 7 moles of water of hydration, preferably 2 to 3 moles of water of hydration.

In the compositions of the invention, it is preferred that for each part by weight of succinyl peroxide there are from about 0.1 to about 12.5 parts by weight of water as water of hydration, and from about 1 to about 50 parts by weight dehydrating agent, more preferably from about 0.4 to about 1 part by weight of water and from about 1 to about 3.5 parts by weight of dehydrating agent, and most preferably from about 0.4 to about 0.7 parts by weight of water and from about 1.1 to about 2.2 parts by weight of dehydrating agent.

The composition of the invention can be prepared by intimately mixing succinyl peroxide, an appropriate dehydrating agent and water. It should be understood that the term dehydrating agent as used herein in connection with the method of the invention refers to either anhydrous dehydrating agent or partially hydrated dehydrating agent. Conveniently the compositions are prepared by mixing the dehydrating agent with a paste of succinyl peroxide in water. Although a paste comprising a mixture of 70% by weight of succinyl peroxide and 30% by weight of water is preferred since such paste is available commercially, pastes having a succinyl peroxide content generally down to about 40% by weight and up to about 90% by weight can, if desired, be employed. Whatever the succinyl peroxide content of the paste, it can be treated to provide a dry mixture by mixing generally with from about 40% to about 95% by weight of dehydrating agent, preferably a sodium or magnesium sulfate as described above, based on the total weight of dehydrating agent and succinyl peroxide paste. Preferably from about 45% to about 80% by weight of dehydrating agent is employed based on the total weight of dehydrating agent and succinyl peroxide paste. Where the dehydrating agent is a partially hydrated material, it is to be understood that the amount employed may have to be increased in proportion to the degree of hydration of the agent.

Preferably the dehydrating agent is employed as a fine powder, and the treatment may be effected by simple mixing for a suitable time to provide a dry mixture. Generally a mixing time of from about 15 minutes to about 6 hours will be sufficient, and typically a mixing time of from about 30 minutes to about 4 hours may be employed.

In the method of the invention, the amount of dehydrating agent and the mixing time generally are adjusted so that there is produced an intimate mixture of ingredients in particulate solid form which gives the appearance of a dry solid, for example, a dry powder. Such a dry solid is a dry mixture of the kind required herein whether or not the mixture as a whole is dry in any absolute sense. Thus, provided any water present is captured by dehydrating agent and is not free to wet the peroxide, the mixture is dry.

In preparing the compositions of the invention, other optional ingredients may be included as and when desired. Thus, the compositions may include one or more detergent materials, chelating agents, hydrogen peroxide donors, e.g., urea hydrogen peroxide adduct or sodium perborate, and coloring agents. For example, the compositions may include from about 1% to about 2% by weight of a solid anionic detergent, e.g. sodium lauryl sulfate, or non-ionic detergent, and color may be provided using either a dyestuff or a pigment, e.g. ultramarine. In particular, the compositions preferably may include a dyestuff (typically one giving a blue color) which is stable in the presence of succinyl peroxide when in aqueous solution at dilutions such as those mentioned below. As an example of such a dyestuff there may be mentioned the copper phthalocyanine complex C.I. Acid Blue 254.

The compositions of the present invention are biocidal, and accordingly are useful as cleaning and/or disinfecting and/or sterilizing and/or antiseptic compositions. The compositions by virtue of the fact that they contain succinyl peroxide are not only bactericidal, but also fungicidal, sporicidal and perhaps virucidal. In particular, the compositions of the invention may be used as general purpose hard surface cleaners, as instrument sterilizers, or as a replacement for iodophors.

Moreover, because the compositions are in a stable dry powder form, they may be packaged for distribution, storage and use without any special restrictions being imposed on transport and storage conditions. As shown below, the compositions remain in active condition even after a storage period well in excess of one year.

In use the compositions are dissolved in water at a high dilution, typically at a dilution of from 0.05% to 2% w/w (based on a succinyl peroxide content of about 20% by weight) and are used immediately after they are made up in diluted form.

Following is a description by way of examples of the preparation of stabilized peroxide compositions in accordance with the invention.

EXAMPLE 1

0.2 kg of a 70% by weight succinyl peroxide paste in water obtained from Laporte Industries was mixed with various proportions of sodium and magnesium sulfate to obtain a dry mixture. The dehydrating agent employed, its amount and the mixing conditions and time are shown in Table 1 below; and the parts by weight of water (as water of hydration) and of dehydrating agent (DA) (anhydrous basis) for each part by weight of succinyl peroxide (SP) in the compositions obtained are given in Table 2.

TABLE 1

| % w/w Succinyl Peroxide as a 70% w/w paste in water | % w/w Magnesium Sulfate Monohydrate | % w/w Sodium Sulfate-Anhydrous | Mixing Conditions | Mixing Time |
|---|---|---|---|---|
| 10 | 90 | — | Tumble mixer | 4 hours |
| 20 | 80 | — | Tumble mixer | 4 hours |
| 30 | 70 | — | Tumble mixer | 4 hours |
| 50 | 50 | — | Tumble mixer | 4 hours |
| 10 | — | 90 | Tumble mixer | 4 hours |
| 20 | — | 80 | Tumble mixer | 4 hours |
| 30 | — | 70 | Tumble mixer | 4 hours |

TABLE 2

| % w/w Succinyl Peroxide as a 70% w/w paste in water | % w/w Magnesium Sulfate Monohydrate | % w/w Sodium Sulfate-Anhydrous | Parts by Weight (SP:Water:DA) |
|---|---|---|---|
| 10 | 90 | — | 1:2.1:11.2 |
| 20 | 80 | — | 1:1.2:5 |
| 30 | 70 | — | 1:0.9:2.9 |
| 50 | 50 | — | 1:0.6:1.2 |
| 10 | — | 90 | 1:0.4:12.9 |
| 20 | — | 80 | 1:0.4:5.7 |
| 30 | — | 70 | 1:0.4:3.3 |

Under storage conditions at ambient temperature each of the above-prepared dry mixtures gave results which indicated that a shelf life in excess of one year can be obtained in accordance with the present invention. In this connection, and by way of example, reference is made to the appended drawing in which the sole FIGURE represents a graph of activity (% w/w of succinyl peroxide) vs. time in days for a 70% by weight succinyl peroxide paste in water compared with two of the dry mixtures prepared as described above. The results expressed graphically were obtained from batches stored at about 20° C., the % w/w of succinyl peroxide being determined by sampling at suitable intervals and estimating the remaining succinyl peroxide by standard iodometric methods.

In the graph, curve A shows the activity of the 70% paste, from which it can be seen that activity decreases to a low level within about 60 days and at about 90 days the activity is so low as to be virtually not measurable. By contrast line B (mixture of 30% w/w of 70% paste with 70% w/w magnesium sulfate monohydrate) and line C (mixture of 30% w/w of 70% paste with 70% w/w anhydrous sodium sulfate) show that in accordance with the present invention activity is maintained at a significant level over a much longer period of time.

EXAMPLE 2

50 parts by weight of a 70% by weight succinyl peroxide paste in water obtained from Laporte Industries were mixed with 50 parts by weight of magnesium sulfate monohydrate to obtain a dry mixture. The initial succinyl peroxide assay given by the dry mixture was 33.3% w/w and after 14 months of storage at ambient temperature the mixture gave a succinyl peroxide assay of 31.6% w/w.

EXAMPLE 3

A large scale batch of 50 kg of a stabilized peroxide composition was prepared by mixing 20 kg of a 70% by weight succinyl peroxide paste in water with 30 kg of magnesium sulfate dihydrate to form a dry mixture. The dry mixture, which for each part by weight of succinyl peroxide contains 0.9 parts by weight of water and 1.7 parts by weight of magnesium sulfate, was then packed as 5 kg lots in polyethylene bags and those in turn were stored in a fiberboard drum.

The initial succinyl peroxide assay given by the dry mixture was 29.0% w/w. After storage at ambient temperature for one month there was an initial drop in the assay to a figure of 27.0% w/w, but after a total of 5 months storage at ambient temperature the succinyl peroxide assay remained at 27.0% w/w.

The compositions of Examples 1 to 3, when prepared in use-dilution in accordance with the method described hereinabove, provided solutions having a pH of about 2.5.

We claim:

1. A stable succinyl peroxide composition comprising in particulate solid form a mixture of succinyl peroxide, a water-soluble dehydrating agent which is unreactive to succinyl peroxide, and water, the water being bound to the dehydrating agent as water of hydration.

2. A composition according to claim 1 wherein for each part by weight of succinyl peroxide there are from about 0.1 to about 12.5 parts by weight of bound water and from about 1 to about 50 parts by weight of the dehydrating agent.

3. A composition according to claim 2 wherein for each part by weight of succinyl peroxide there are from about 0.4 to about 1 part by weight of bound water and from about 1 to about 3.5 parts of the dehydrating agent.

4. A composition according to claim 3 wherein for each part by weight of succinyl peroxide there are from about 0.4 to about 0.7 part by weight of bound water and about 1.1 to about 2.2 parts by weight of the dehydrating agent.

5. A composition according to claim 1 wherein the dehydrating agent is an inorganic compound.

6. A composition according to claim 5 wherein the dehydrating agent is magnesium sulfate or sodium sulfate.

7. A composition according to claim 6 wherein the dehydrating agent is magnesium sulfate.

8. A composition according to claim 7 wherein each mole of magnesium sulfate has bound thereto from 2 to less than 7 moles of water of hydration.

9. A composition according to claim 8 wherein each mole of magnesium sulfate has bound thereto from 2 to 3 moles of water of hydration.

10. A composition according to claim 6 wherein for each part by weight of succinyl peroxide there are from about 0.1 to about 12.5 parts by weight of bound water and from about 1 to about 50 parts by weight of the dehydrating agent.

11. A composition according to claim 10 wherein for each part by weight of succinyl peroxide there are about 1.2 parts by weight of bound water and 5 parts by weight of magnesium sulfate.

12. A composition according to claim 10 wherein for each part by weight of succinyl peroxide there are from about 0.4 to about 1 part by weight of bound water and from about 1 to about 3.5 parts of the dehydrating agent.

13. A composition according to claim 12 wherein for each part by weight of succinyl peroxide there are about 0.9 parts by weight of bound water and about 1.7 parts by weight of magnesium sulfate.

14. A composition according to claim 12 wherein for each part by weight of succinyl peroxide there are about 0.9 part of bound water and about 2.9 parts of magnesium sulfate.

15. A composition according to claim 12 wherein for each part by weight of succinyl peroxide there are about 0.4 part of bound water and about 3.3 parts of sodium sulfate.

16. A composition according to claim 12 wherein for each part by weight of succinyl peroxide there are from about 0.4 to about 0.7 part of bound water and from about 1.1 to about 2.2 parts of the dehydrating agent.

17. A composition according to claim 16 wherein for each part of succinyl peroxide there are about 0.6 part of bound water and about 1.2 parts of magnesium sulfate.

18. A method for preparing a stable succinyl peroxide composition comprising in particulate solid form a mixture of succinyl peroxide, a water-soluble dehydrating agent which is unreactive to succinyl peroxide, and water, the water being bound to the dehydrating agent as water of hydration, which method comprises mixing a succinyl peroxide paste consisting of succinyl peroxide and water with a water-soluble dehydrating agent selected from the group consisting of anhydrous dehydrating agent and partially hydrated dehydrating agent, the dehydrating agent being mixed with the succinyl peroxide paste in an amount and for a time sufficient to bind all of the water in the paste and provide a dry mixture.

19. A method according to claim 18 wherein the dehydrating agent employed is an inorganic compound.

20. A method according to claim 19 wherein from about 40% to about 95% by weight of the dehydrating agent based on the total weight of the dehydrating agent and the paste is employed.

21. A method according to claim 20 wherein the paste comprises about 70% by weight of succinyl peroxide and about 30% by weight of water.

22. A method according to claim 19 wherein the dehydrating agent employed is selected from the group consisting of anhydrous magnesium sulfate, anhydrous sodium sulfate, a partial hydrate of magnesium sulfate and a partial hydrate of sodium sulfate.

23. A method according to claim 22 wherein the paste comprises about 70% by weight of succinyl peroxide and about 30% by weight of water.

24. A method according to claim 23 wherein from about 40% to about 95% by weight of the dehydrating agent based on the total weight of the dehydrating agent and the paste is employed.

25. A method according to claim 24 wherein from about 45% to about 80% by weight of the dehydrating agent based on the total weight of the dehydrating agent and the paste is employed.

26. A method according to claim 22 wherein the dehydrating agent employed is anhydrous magnesium sulfate or a partial hydrate of magnesium sulfate.

27. A method according to claim 26 wherein the paste comprises about 70% by weight of succinyl peroxide and about 30% by weight of water.

28. A method according to claim 27 wherein about 40% to about 95% by weight of the dehydrating agent based on the total weight of the dehydrating agent and the paste is employed.

29. A method according to claim 28 wherein about 45% to about 80% by weight of the dehydrating agent based on the total weight of the dehydrating agent and the paste is employed.

30. A method according to claim 26 wherein the dehydrating agent employed is magnesium sulfate monohydrate or magnesium sulfate dihydrate.

31. A method according to claim 30 wherein the paste comprises about 70% by weight of succinyl peroxide and about 30% by weight of water.

32. A method according to claim 31 wherein from about 40% to about 95% by weight of the dehydrating agent based on the total weight of the dehydrating agent and the paste is employed.

33. A method according to claim 32 wherein from about 45% to about 80% by weight of the dehydrating agent based on the total weight of the dehydrating agent and the paste is employed.

* * * * *